(12) United States Patent
Lederman

(10) Patent No.: US 6,210,318 B1
(45) Date of Patent: Apr. 3, 2001

(54) STENTED BALLOON PUMP SYSTEM AND METHOD FOR USING SAME

(75) Inventor: David M. Lederman, Marblehead, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/264,943

(22) Filed: Mar. 9, 1999

(51) Int. Cl.[7] ....................................... A61M 1/12
(52) U.S. Cl. .............................................. 600/18
(58) Field of Search ........................... 600/16–18; 623/3, 623/3.1, 3.16, 3.2, 3.21

(56) References Cited

U.S. PATENT DOCUMENTS

| | | |
|---|---|---|
| 3,657,744 | 4/1972 | Ersek . |
| 4,077,394 | 3/1978 | McCurdy . |
| 4,080,958 | 3/1978 | Bregman et al. . |
| 4,154,227 | 5/1979 | Krause et al. . |
| 4,407,271 | 10/1983 | Schiff . |

(List continued on next page.)

FOREIGN PATENT DOCUMENTS

| | | |
|---|---|---|
| 0194338 | 9/1986 | (EP) . |
| 9818508 | 5/1998 | (WO) . |

*Primary Examiner*—George R. Evanisko
(74) *Attorney, Agent, or Firm*—Nutter, McClennen & Fish, LLP; Thomas J. Engellenner; Ronald E. Cahill

(57) ABSTRACT

A balloon pump system including catheter-mounted pumping balloon configured to be positioned within a desired body passageway to pump a fluid through the body passageway. A stent is percutaneously deployed within the body passageway. The pumping balloon is percutaneously deployed within the stent such that the stent is interposed between the pumping balloon and the walls of the body passageway. The stent substantially limits the compliance of the body passageway, preventing the passageway in the vicinity of the pumping balloon from significantly expanding or contracting in response to forces generated by inflation and deflation of the pumping balloon. As a result, a volume of fluid substantially equivalent to a change in volume of the pumping balloon is displaced when the pumping balloon is inflated or deflated.

31 Claims, 3 Drawing Sheets

U.S. PATENT DOCUMENTS

| | | |
|---|---|---|
| 4,522,195 | 6/1985 | Schiff . |
| 4,546,759 | 10/1985 | Solar . |
| 4,580,568 | 4/1986 | Gianturco . |
| 4,655,771 | 4/1987 | Wallsten . |
| 4,692,148 | 9/1987 | Kantrowitz et al. . |
| 4,697,574 | 10/1987 | Karcher et al. . |
| 4,733,665 | 3/1988 | Palmaz . |
| 4,743,251 | 5/1988 | Barra . |
| 4,776,337 | 10/1988 | Palmaz . |
| 4,785,795 | 11/1988 | Singh . |
| 4,800,882 | 1/1989 | Gianturco . |
| 4,830,003 | 5/1989 | Wolff et al. . |
| 4,856,516 | 8/1989 | Hillstead . |
| 4,886,062 | 12/1989 | Wiktor . |
| 4,902,272 | 2/1990 | Milder et al. . |
| 4,950,227 | 8/1990 | Savin et al. . |
| 4,954,126 | 9/1990 | Wallstén . |
| 4,969,458 | 11/1990 | Wiktor . |
| 4,994,071 | 2/1991 | MacGregor . |
| 5,037,427 | 8/1991 | Harada et al. . |
| 5,041,126 | 8/1991 | Gianturco . |
| 5,061,275 | 10/1991 | Wallstén . |
| 5,071,407 | 12/1991 | Termin et al. . |
| 5,089,005 | 2/1992 | Harada . |
| 5,135,536 | 8/1992 | Hillstead . |
| 5,161,547 | 11/1992 | Tower . |
| 5,163,952 | 11/1992 | Froix . |
| 5,197,978 | 3/1993 | Hess . |
| 5,217,483 | 6/1993 | Tower . |
| 5,316,023 | 5/1994 | Palmaz et al. . |
| 5,342,387 | 8/1994 | Summers . |
| 5,360,443 | 11/1994 | Barone et al. . |
| 5,383,892 | 1/1995 | Cardon et al. . |
| 5,443,498 | 8/1995 | Fontaine . |
| 5,480,423 | 1/1996 | Ravenscroft et al. . |
| 5,527,354 | 6/1996 | Fontaine et al. . |
| 5,591,226 | 1/1997 | Trerotola et al. . |
| 5,609,626 | 3/1997 | Quijano et al. . |
| 5,628,755 | 5/1997 | Heller et al. . |
| 5,632,760 | 5/1997 | Sheiban et al. . |
| 5,632,762 | 5/1997 | Myler . |
| 5,634,928 | 6/1997 | Fischell et al. . |
| 5,639,274 | 6/1997 | Fischell et al. ................ 604/96 |
| 5,645,560 | 7/1997 | Crocker et al. ................ 606/192 |
| 5,653,736 | 8/1997 | Glastra . |
| 5,690,642 | 11/1997 | Osborne et al. . |
| 5,693,085 | 12/1997 | Buirge et al. . |
| 5,695,516 | 12/1997 | Fischell et al. . |
| 5,695,517 | 12/1997 | Marin et al. . |
| 5,702,419 | 12/1997 | Berry et al. . |
| 5,707,354 | 1/1998 | Salmon et al. . |
| 5,725,519 | 3/1998 | Penner et al. . |
| 5,725,535 | 3/1998 | Hegde et al. . |
| 5,730,698 | 3/1998 | Fischell et al. . |
| 5,733,330 | 3/1998 | Cox . |
| 5,735,869 | 4/1998 | Fernandez-Aceytuno . |
| 5,743,874 | 4/1998 | Fischell et al. . |
| 5,749,848 | 5/1998 | Jang et al. . |
| 5,749,851 | 5/1998 | Wang . |
| 5,766,239 | 6/1998 | Cox . |
| 5,820,542 * | 10/1998 | Dobak, III et al. ................ 600/16 |
| 5,827,171 | 10/1998 | Dobak, III et al. . |

* cited by examiner

STENTED BALLOON PUMP SYSTEM AND METHOD FOR USING SAME

BACKGROUND OF THE INVENTION

1. Field of the Invention

The present invention relates generally to pumping balloons and, more particularly, to temporary cardiac support systems.

2. Related Art

There are a number of medical conditions in which it is necessary or desirable to aid blood flow in a patient. For example, during the performance of surgical procedures such as certain types of open heart surgery, external means are required to completely assume the blood pumping function of the heart to maintain adequate circulation to body organs such as the brain and the heart itself. In other situations, body organs require blood flow which the body is incapable of sufficiently providing due to a failing, traumatized or infarcted heart.

It has been recognized that in these and other situations, it is preferable to have blood pumped in a pulsatile manner, similar to the pumping action of the normal heart. A common approach has been to provide cardiac assistance by introducing a balloon into the circulatory system, commonly the thoracic aorta, and causing the balloon to cyclically inflate and deflate in some relationship with the rhythm of the patient's heart. Such cardiac assist systems of this type are commonly used to assist the left ventricle of the heart, which bears the primary responsibility for systemic circulation, and is most frequently in need of assistance. The most common configuration of the pumping cycle is the "counterpulsation" mode, in which the pumping balloon is inflated during the diastolic portion of the natural cycle to increase blood pressure, and deflated during the systolic portion of the natural cycle to decrease blood pressure and resistance to the left ventricle's natural pumping action. This reduces the load on the left ventricle and raises aortic pressure to increase the blood flow to the coronary and carotid arteries.

Such cardiac assist systems are commonly used due to the limited trauma associated with their implementation. The pumping balloon is generally implemented as a collapsible structure that can be introduced into any large artery, such as a femoral, as part of a standard catheterization procedure. Once introduced into the circulatory system, the pumping balloon is guided into a desired location of the circulatory system. As such, implementation of cardiac assist pumping balloons generally do not require major thoracic or otherwise invasive surgery. Exemplary conventional cardiac assist systems of this type are disclosed in U.S. Pat. Nos. 4,080,958, 4,692,148, 4,077,394, 4,154,227, 4,522,195, 4,407,271 and 4,697,574, the disclosures of which are hereby incorporated by reference herein in their entirety.

U.S. Pat. Nos. 5,820,542 and 5,827,171 disclose various complex designs for intravascular circulatory assist devices involving a pumping membrane such as an inflatable balloon, disposed within an expandable housing structure such as another balloon. The pumping membrane thus divides the outer housing into an intermediate control chamber and an interior pumping chamber. Injection and evacuation of a control/fluid into the control chamber deflates (pumps) and inflates (refills) the pumping chamber. Expandable and collapsible stents are disclosed as one mechanism to expand and retain the control chamber in its maximum dimension while control fluid is withdrawn.

U.S. Pat. Nos. 4,902,272 and 4,785,795 represent important advances in the art of cardiac support systems. Unlike the above cardiac assist systems that adjust systemic pressure to assist a natural heart, these latter patents disclose apparatuses and techniques for directly pumping blood. U.S. Pat. No. 4,902,272 discloses a catheter-based intra-arterial cardiac support system that includes one or two valves that are mounted upstream and downstream of a cyclically inflatable pumping balloon synchronized with the cardiac cycle. One disclosed embodiment provides assistance to the left ventricle through the placement of the pumping balloon in the descending aorta with a balloon valve located distally relative to the natural heart. The balloons are individually inflated and deflated to directly pump blood. The pumping action is peristaltic in nature and operated in phased relationship to the systole and diastole of the natural heart.

U.S. Pat. No. 4,785,795 discloses a catheter-based, high-frequency intra-arterial cardiac support system that includes an externally controlled pumping balloon and balloon valve. The pumping balloon and valve are positioned in a major artery downstream of a natural heart, and are operated at a pumping frequency that is at least three times the normal frequency of the heart to directly pump blood. To assist a left ventricle, for example, the balloon pump is located in the ascending aorta between the aortic valve and the ostium innominate artery. The pumping balloon and valve are sequentially operated to pump blood from the left ventricle into the arterial tree. To assist the right ventricle, the pumping balloon is located in the pulmonary track immediately downstream from the pulmonary valve. The pumping balloon and valve are sequentially operated to pump blood from the right ventricle into the pulmonary trunk. In each application, the balloon valve is positioned downstream of the pumping balloon; that is, the pumping balloon is positioned between the balloon valve and the natural aortic or pulmonary valve.

Although these approaches overcome the above-noted drawbacks associated with traditional cardiac assist systems by directly pumping blood to support or replace the pumping action of the heart, they too have limits to their effectiveness. Unlike conventional pumping balloons, these latter two approaches operate with the pumping balloon interposed between two valves in an otherwise closed region of the circulatory system. The valves may be natural or balloon valves, depending on the embodiment of the cardiac support system. The inventor has observed that at times during certain operations of such devices, the surrounding valves simultaneously occlude the vessel at least momentarily while the pumping balloon deflates. Such an occurrence creates temporarily a vacuum within the vessel region. At times this vacuum is sufficient to draw the vessel walls inward with the deflating pumping balloon. This reduces the effective pumping displacement of the pumping balloon, thereby reducing the overall effectiveness of these cardiac support systems.

SUMMARY OF THE INVENTION

The present invention is a stented balloon pump system and method for using the same. Apparatus embodiments of the present invention include a catheter-mounted pumping balloon configured to be positioned within a desired body passageway to propel; that is, pump directly a fluid through the body passageway. In accordance with the present invention, a stent is deployed within the body passageway. Such direct pumping activity applies radial forces to the surrounding vessel which are substantially greater than those provided by conventional systems that adjust systemic pressure. A pumping balloon subsequently deployed within the stent such that the stent is interposed between the pumping balloon and the body passageway within which the pumping balloon is operatively positioned. The stent substantially limits the compliance of the body passageway in the vicinity of the pumping balloon, preventing the passageway from significantly expanding or contracting in response to forces generated by inflation and deflation of the pumping balloon. As a result, a volume of fluid substantially equivalent to a change in volume of the pumping balloon is displaced when the pumping balloon is inflated or deflated. Method embodiments of the present invention include reducing the compliance of a body passageway through the surgical or percutaneous deployment of a stent suitable for the selected body passageway. A pumping balloon is subsequently deployed so as to be operatively positioned within the body passageway in which the stent is located. The pumping balloon is operated to pump fluid in a desired direction through the body passageway. Significantly, by limiting the compliance of the selected body passageway, the present invention enables a pumping balloon to achieve high pumping efficiency and throughput.

The balloon pump system may also include one or more collapsible and erectable valves operatively coupled to the catheter adjacent to the pumping balloon. The valves may be passive or active valves controlled in the same or different manner than the pumping balloon. For example, the balloon pump and valves, if any, may be controlled fluidically through a multi-lumen catheter or by some other means, such as through electrical, electro-mechanical or mechanical means. Certain embodiments include an extracorporeal controller operatively coupled to the catheter for controlling inflation and deflation of the pumping balloon and to control the extension and collapse of the active valves, if any. The stent may be a permanent stent and has a length sufficient to surround at least the pumping balloon. In alternative embodiments, the stent may also enclose one or two valves, if present.

Various aspects and embodiments of the present invention provide certain advantages. Not all aspects and embodiments of the invention share the same advantages and those that do may not share them under all circumstances. This being said, embodiments of the present invention provide numerous advantages, including the noted advantage of limiting the adverse effect of vessel compliance on pumping balloon throughput and efficiency. Further features and advantages of the present invention as well as the structure and operation of various aspects and embodiments of the present invention are described in detail below with reference to the accompanying drawings.

BRIEF DESCRIPTION OF THE DRAWINGS

The present invention is pointed out with particularity in the appended claims. The above and further advantages of this invention may be better understood by referring to the following description when taken in conjunction with the accompanying drawings, in which like reference numerals designate like elements. In the drawings, dimensions such as thickness have been exaggerated in the interest of clarity. In the drawings:

DETAILED DESCRIPTION

Figure 1:
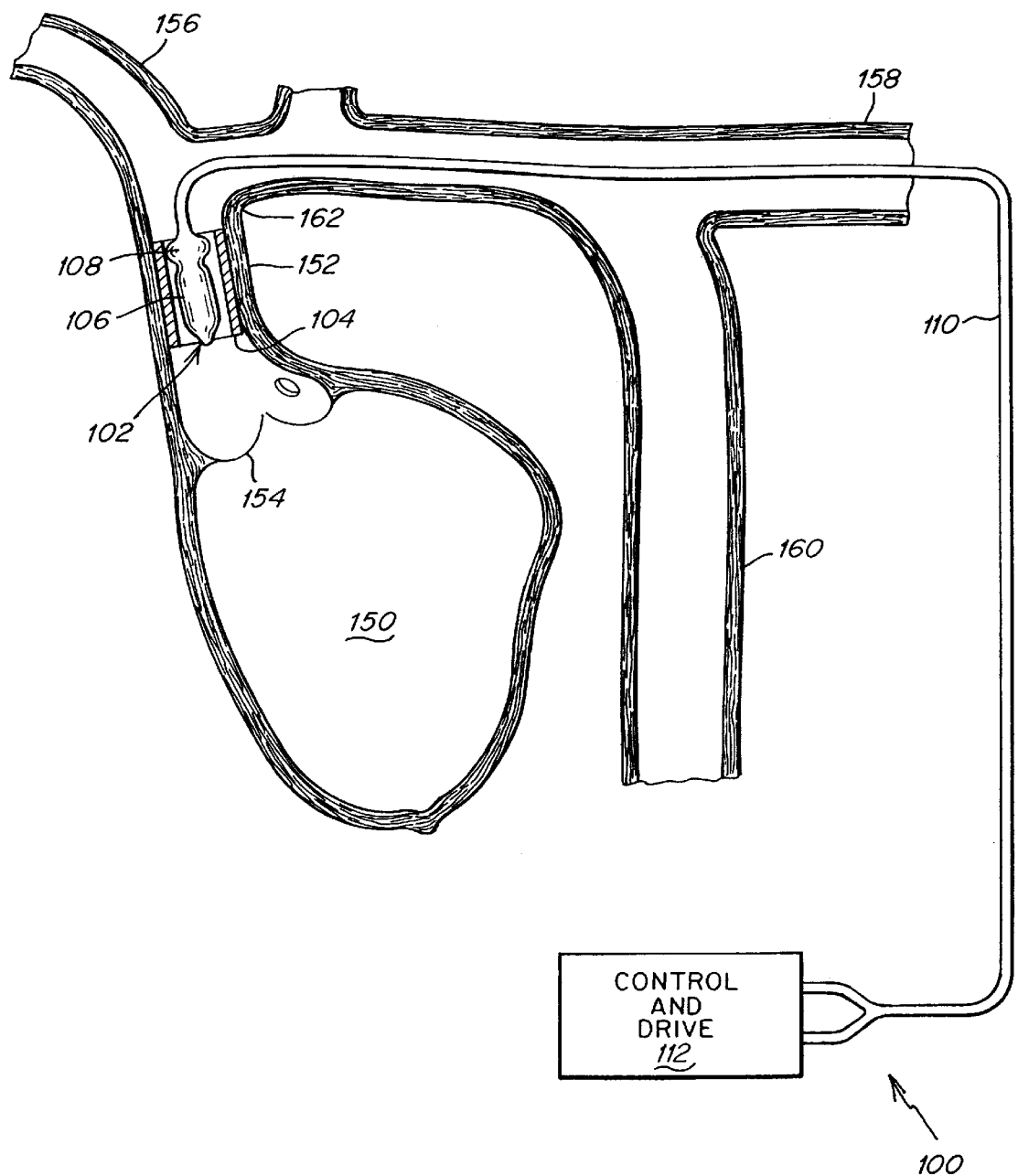
FIG. 1 is a schematic view of one embodiment of the balloon pump system of the present invention implemented as a cardiac support system located in the ascending aorta to provide direct, extracorporealy controlled blood pumping assistance to a left ventricle of a natural heart.

As noted, although commonly used, cardiac assist balloon systems that adjust systemic pressure provide limited pumping assistance to the natural heart. Recent advances, in particular the direct pump support systems disclosed in U.S. Pat. Nos. 4,902,272 and 4,785,795, provide direct blood pumping support. Although not a significant contributing or recognized problem in pressure-adjusting cardiac assist systems, vessel compliance adversely affects the efficiency of direct pumping systems. In such cardiac systems, the vessel may be constricted due to the vessel wall adhering to a rapidly deflating pumping balloon. This reduces the volume of blood displaced by the pumping balloon when inflated. Traditional techniques that are directed to adjusting systemic pressure to assist the natural heart have not addressed or considered the elastic compliance of vessel walls, primarily due to the fact that vessel compliance has traditionally contributed minimally to the efficiency losses experienced by such systems. Additional causes may include the often advanced accumulation of atherosclerotic plaques or other conditions which reduce vessel compliance in the patients receiving these conventional treatments. Despite the limited significance attributed to vessel compliance heretofore, the inventor has determined that vessel compliance contributes significantly to a reduction in throughput in direct blood pump systems despite the onset of such conditions.

The present invention is directed to a stented balloon pump system and method for using the same. Generally, the balloon pump system includes a catheter-mounted pumping balloon constructed and arranged to be positioned within a desired body passageway. A stent suitable for the selected body passageway is surgically or percutaneously deployed prior to or with the pumping balloon into the selected desired region of the body passageway. The pumping balloon is subsequently deployed by catheter introduction so as to be positioned within the stent; that is, the stent is interposed between the balloon pump and the body passageway within which the balloon pump is operatively positioned. The stent is constructed so as to substantially limit the compliance of the selected body passageway region, preventing the passageway walls in the vicinity of the pumping balloon from significantly expanding or contracting in response to forces generated by inflation and deflation of the pumping balloon. As a result, a volume of fluid substantially equivalent to a change in volume of the pumping balloon is displaced during each pumping balloon inflation/deflation cycle. The balloon pump system of the present invention thereby provides for efficient direct pumping of a fluid through the body passageway. The substantial elimination of the counterproductive phenomena associated with vessel compliance therefore represents a significant advance in the art. In particular, when implemented as a cardiac support system for directly pumping blood, the present invention represents a potentially dramatic positive impact on medical assistance which can be provided to body organs including but not limited to a failing, traumatized or infarcted heart, or to maintain adequate circulation during the performance of a surgical procedure.

As will become apparent from the following description, the present invention may be used in any body passageway.

Thus, as used herein, "body passageway" means pertaining to, composed of, or provided with arteries, veins and other vessels, ducts, etc., which convey blood, lymph, gas or other fluids. For ease of description, the present invention is described primarily with respect to a cardiac support balloon pump system deployed within the circulatory system for assisting circulation due to a failing, traumatized or infarcted heart, or to assist circulation during the performance of a surgical procedure. However, it should be understood that the present invention may also be introduced into and utilized within any other body passageway to assist in the transport of any fluid therethrough.

FIG. 1 is a schematic view of one exemplary embodiment of the balloon pump system of the present invention. In this particular illustrative embodiment, the balloon pump system is implemented as a cardiac support system located in ascending aorta 152 between aortic valve 154 and ostium of innominate artery 156 to provide extracorporeal controlled balloon pumping to assist left ventricle 150. In accordance with the present invention, and as shown in the exemplary embodiment of FIG. 1, balloon pump system 100 includes at least a catheter-mounted balloon 102 operatively located within a stent 104. In the illustrative embodiments, balloon pump 102 includes a pumping balloon 106 and a balloon valve 108 operatively located adjacent to pumping balloon 104. The balloon valve 106 is mounted downstream of pumping balloon 106. As such, pumping balloon 106 is operatively positioned between aortic valve 154 and balloon valve 108. Balloon pump 102 is attached to a multi-lumen catheter 110 which is brought outside the body through the arterial tree, such as the subclavian artery 158, as shown in FIG. 1.

In the illustrative embodiment shown in FIG. 1, balloon pump 102 is preferably a high-frequency balloon pump constructed and operated as disclosed in commonly owned U.S. Pat. No. 4,785,795 to Singh, the disclosure of which is hereby incorporated by reference herein in its entirety. As described therein, a high frequency pumping balloon is positioned in a major artery immediately adjacent to the heart. As shown in this exemplary embodiment and described in greater detail in the '795 patent, balloon pump 102 is located in the ascending aorta 152 to provide extracorporeal controlled balloon pumping to assist left ventricle 150. It should be understood that the present invention, when implemented as a cardiac support system, may be operatively positioned in other locations of the circulatory system. For example, embodiments of the cardiac support system may be located in the pulmonary tract immediately downstream of the pulmonary valve to assist the right ventricle, as described in the '795 patent. In this embodiment, the catheter is preferably placed in the venous system, leading out through the right ventricle and superior vena cava and a brachycephalic vein. In an alternative embodiment, the balloon pump may be constructed and operated as described in commonly owned U.S. Pat. No. 4,902,272 to Milder et al., the disclosure of which is also hereby incorporated by reference in its entirety. In this embodiment, the balloon pump is located in the descending aorta 160 to assist the left ventricle 150. As will be described in detail below, in this embodiment the balloon pump 102 is preferably implemented with two valves operatively mounted on opposing sides of pumping balloon 106.

Referring again to the exemplary embodiment illustrated in FIG. 1, balloon pump 106 and balloon valve 108 are attached to a control drive mechanism 112 via multi-lumen catheter 110. Typically, control drive mechanism 112 is located outside the body, and multi-lumen catheter 110 is introduced into the body via a blood vessel such as subclavian artery 158. As noted, in other applications, catheter 110 may be introduced into the body via other blood vessels such the femoral artery. In alternative embodiments, control drive mechanism 112 may be located within the body. In such embodiments, catheter 110 need not extend outside the body.

Control drive mechanism 112 cyclically and individually inflates pumping balloon 106 and, in the illustrative embodiment, balloon valve 108, with respect to one another and with respect to the diastole and systole of the patient's heart, as described in the '795 and, alternatively, the '272 patent incorporated by reference above. The high frequency pumping action of balloon pump 102 is timed to increase blood flow towards aortic root 162 during systole and away from aortic root 162 during diastole. Preferably, pumping balloon 106 pumps with a frequency up to several times that of left ventricle 150, as described in the '795 patent.

Control drive mechanism 112 is generally calibrated based on an input signal which indicates when the systolic and diastolic periods of the patient's heartbeat begin. This signal may be taken, for example, from the R wave of an electrocardiograph, although numerous other approaches may be used. In other cases, when the patient's heartbeat is regulated by a pacemaker, the signals indicative of systolic and diastolic periods may be obtained directly from the pacemaker itself. Further, if obtaining electric timing signals proves to be particularly troublesome, signals for the timing of the control unit may be obtained from arterial or ventricular pressure waveforms or other characteristics indicative of the natural rhythm of the heart. It should be understood that balloon pump 102 may be controlled in any manner now or later developed to achieve a desired pumping action for the selected body passageway and fluid, and therefore, is not described further herein.

As noted, in accordance with the present invention, pumping balloon 106 is operatively located within a stent 104 deployed at a desired location of the body passageway. Stent 104 reduces compliance of the wall of the body passageway in contact with and immediately adjacent to stent 104. This substantially prevents such portions of the vessel wall from expanding or contracting in response to forces generated by inflation and deflation of pumping balloon 106. Exemplary embodiments of balloon pump 102 and stent 104 will now be described with reference to FIGS. 2A, 2B, 3A and 3B.

Figure 2A:
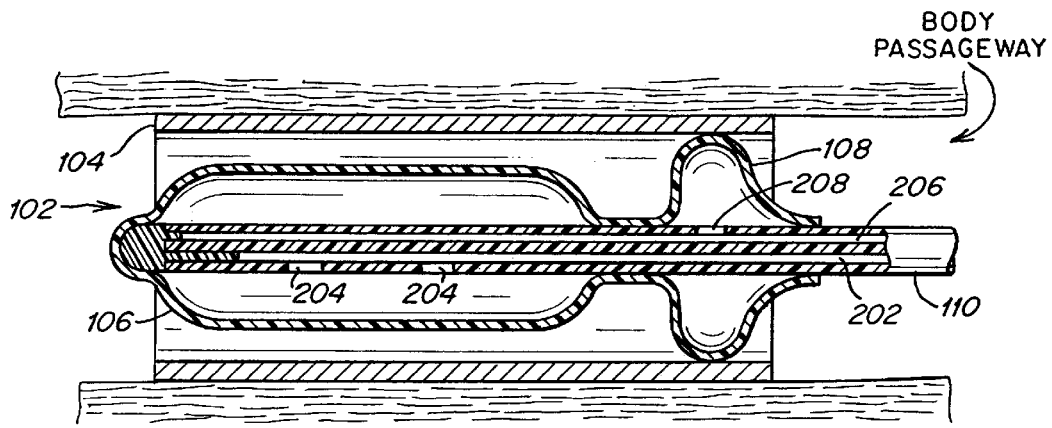
FIG. 2A is a cross-sectional view of one embodiment of the balloon pump and stent illustrated in FIG. 1.
Figure 2B:
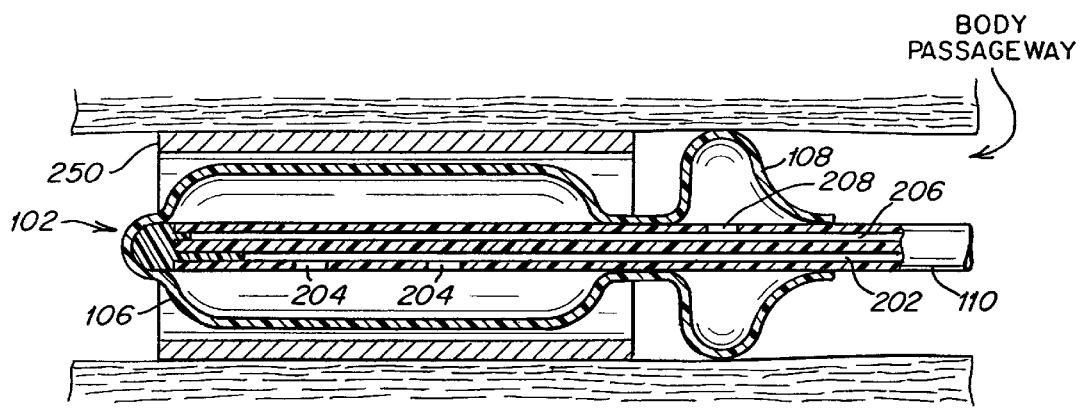
FIG. 2B is a cross-sectional view of an alternative embodiment of the balloon pump and stent.

FIG. 2 is a cross-sectional view of an exemplary single valve embodiment of the balloon pump 102 illustrated in FIG. 1. In this illustrative embodiment, stent 104 has a length sufficient to enable pumping balloon 106 and balloon valve 108 to be operatively positioned within its hollow bore. FIG. 2B is a cross-sectional view of an alternative embodiment of a balloon pump and stent In this embodiment, the stent has a length sufficient to enable only pumping balloon 106 to be operatively positioned in its hollow bore. Alternatively, it may be preferable to provide the stent with a length sufficient to enclose both the balloon pump and associated balloon valves.

Figure 3A:
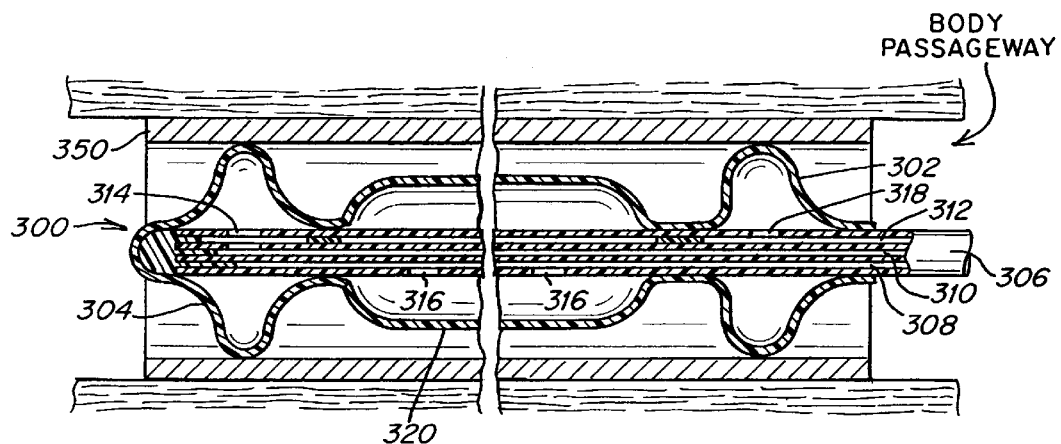
FIG. 3A is a cross-sectional view of a further embodiment of the balloon pump and stent of the present invention.
Figure 3B:
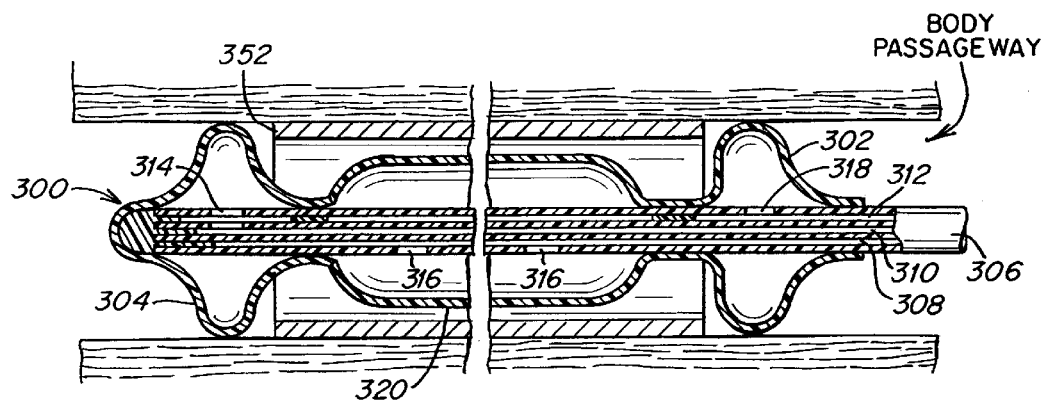
FIG. 3B is a cross-sectional view of a still further embodiment of the balloon pump and stent.

FIGS. 3A and 3B illustrate an alternative embodiment of the balloon pump. In these illustrative embodiments, the balloon pump includes two balloon valves. In the embodiment illustrated in FIG. 3A, the stent is sufficiently long to enable both balloon valves and the pumping balloon to be operatively positioned within its hollow bore. In the embodiment illustrated in FIG. 3B, the stent is only long enough to enable the pumping balloon to be positioned within its bore. As will be described in detail below, the stent 104 may be any stent now or later developed suitable for sufficiently reducing the compliance of the desired body passageway when subject to forces generated by the pumping balloon. Since there are a myriad of stents which may be used depending on the type and condition of the selected body passageway, the structure and operation of the balloon pump, the fluid that is transported through the passageway as well as the manner in which the balloon pump is controlled, stent 104 is shown schematically in the Figures.

Pumping balloon 106 may be any suitable balloon pump now or later developed. In certain preferred embodiments, the balloons of U.S. Pat. Nos. 4,902,272 and 4,785,795, are used. Alternatively, the inflatable device tip of U.S. Pat. No. 4,154,227, the inflatable balloons of U.S. Pat. Nos. 4,697, 574, 5,725,535 and 5,730,698, or the intra-aortic balloon apparatus of U.S. Pat. No. 4,692,148 may be used. All of the above patents are hereby incorporated by reference herein in their entirety. In additional alternative embodiments, pumping balloon 106 may be any device capable of inflation and deflation in response to control system 112. In the exemplary embodiments set forth herein, control system 112 controls the inflation and deflation of pumping balloon 106 by pumping fluid through multi-lumen catheter 110.

Catheter 110 may contain any appropriate number of lumens suitable for the intended application, as should be apparent from this disclosure. Referring to this single valve embodiment illustrated in FIGS. 2A and 2B, the interior of pumping balloon 106 is connected fluidically to one lumen 202 of catheter 110 by hole(s) 204. Similarly, the interior of balloon valve 108 is connected fluidically to lumen 206 of catheter 110 by hole(s) 208. Hole(s) 204 and 208 may be dimensioned to effectuate inflation and deflation of a desired rapidity. Any appropriate fluid or gas may be used to inflate and deflate pumping balloon 14 and balloon valve 15. In a preferred embodiment, however, a low molecular weight gas such as argon is utilized. In another embodiment, helium gas may be used as the drive fluid, as disclosed in U.S. Pat. No. 4,785,795.

As shown in FIGS. 3A and 3B, alternative embodiments of the present invention include two balloon valves 302, 304 mounted on a multi-lumen catheter 306. In this embodiment, catheter 306 contains three lumens 308, 310, 312 fluidically connected to pumping balloon 312, distal balloon valve 304, and proximal balloon valve 302, respectively, by holes 316, 314 and 318, respectively.

It should be understood that control system 112 may control the inflation and deflation of pumping balloon 106 using other techniques now or later developed. For example, in alternative embodiments, control system 112 controls pumping balloon 106 via well known electrical techniques, with pumping balloon 106 including the appropriate devices to inflate and deflate balloon pump 106 in response to predetermined electrical control signals. Alternatively, electro-mechanical or mechanical means may be utilized.

In all of the illustrative embodiments, balloon valves 108, 304 and 302 may be constructed and operated in any desired manner to directly pump fluid through the desired body passageway. As noted, in one preferred embodiment, the balloon valves are controlled as described in U.S. Pat. No. 4,785,795. In another preferred embodiment, the balloon valves are constructed and operated as described in U.S. Pat. No. 4,902,272. In alternative embodiments, balloon valve 108 may be replaced by any valve known in the art, such as the umbrella-like members disclosed in U.S. Pat. No. 4,407, 271, or the flexible canopy disclosed in U.S. Pat. No. 4,785,795. The U.S. Pat. No. 4,407,271 patent is hereby incorporated by reference herein in its entirety. Further, the implemented balloon valves may be controlled (active) or uncontrolled (passive) balloon valves and, if active, may be controlled utilizing the same or different means than that used to control pumping balloon 106. In another aspect of the present invention, pumping balloon 102 does not include any valves.

When fully inflated, pumping balloon 106 and balloon valve 108, 302, 304 have an outer diameter approximately equal to the inner diameter of selected body passageway (ascending aorta 152 in FIG. 1). This enables pumping balloon 106 and pumping valve 108 to substantially occlude the selected body passageway when fully inflated. For the embodiments illustrated in FIGS. 2A and 3A in which the single or dual balloon valve(s) are operatively positioned within stent 104, the outer diameter of the balloon valve, when fully inflated, is approximately equal to the inner diameter of stent 104, 350.

In embodiments of the present invention that are implemented as a cardiac support system, numerous vascular and intra-aortic stents, such as those commercially available from Cordis Corporation, an affiliate of Johnson & Johnson; Boston Scientific Corporation or its affiliate Scimed Life Systems, Inc; Medtronic, Inc.; Guidant Corporation or its affiliate, Advanced Cardiovascular Systems, Inc.; and others, may be used. In one particular embodiment, stent 104 is a substantially cylindrical endoprosthesis device made of wire or filament such as the stent disclosed in U.S. Pat. No. 5,135,536. In an alternative embodiment, endovascular stents used to reinforce body passageways, particularly blood vessels may be used. For instance, the reinforcing stent constructed from a single elongated wire disclosed in U.S. Pat. No. 4,856,516, the stent formed of half-round wire disclosed in U.S. Pat. No. 5,527,354, the collagen-coated stent disclosed in U.S. Pat. No. 5,693,085, the cylindrical, open-ended intra coronary stent disclosed in U.S. Pat. No. 4,969,458, the radially-expandable stent disclosed in U.S. Pat. No. 5,161,547, the balloon-expandable, crush-resistance locking stent disclosed in U.S. Pat. Nos. 5,766, 239 and 5,733,330, the compressive stent disclosed in U.S. Pat. No. 4,830,003, the intravascular radiallyexpandable stent disclosed in U.S. Pat. No. 4,886,062, the expandable intraluminal graft disclosed in U.S. Pat. No. 4,776,337, the expandable polymeric stent disclosed in U.S. Pat. No. 5,163, 952, the stent disclosed in U.S. Pat. No. 5,342,387, the endovascular stent disclosed in U.S. Pat. No. 4,580,568, the vascular stent disclosed in U.S. Pat. No. 5,443,498, the vascular prosthesis stent disclosed in U.S. Pat. No. 5,527, 354, and the self-expanding prosthesis stent disclosed in U.S. Pat. No. 5,061,275, may be used. It may be desirable to provide the stent with a thin graft material covering or lining, such as thinly woven polyester yarns shaped into tubular coverings to form aortic stented grafts of the type commercially available from Boston Scientific Corporation and its affiliate, Meadox Medicols, Inc. The disclosure of all the above patents are hereby incorporated by reference herein in their entirety.

Stent 104 may be percutaneously deployed into the body using any well known apparatus and technique now or later developed. For instance, U.S. Pat. Nos. 4,950,227, 5,480, 423, 5,163,952, 4,969,458, and 5,037,427 disclose various stent delivery systems and methods which may be utilized by the present invention. These and other commercially available from the above-noted and other providers may be used. As is well known in the art, vascular stents are typically deployed in a radially contracted state, and are subsequently expanded after placement within a desired body passageway. Expansion of the stent is often effected by inflation of an angioplasty balloon or the like within the stent, to force radial expansion of the stent until it contacts and/or adheres to the wall of the body passageway. In one embodiment of the present invention, pumping balloon 106 may be inflated within radially contracted stent 104, expanding stent 104 until it contacts the inner wall of descending aorta 152 and embeds itself therein. In an alternative embodiment, another balloon may be used for this purpose. If desired, the above noted stented aortic graft systems can be used, wherein the stent provides a scaffold-like support which can be expanded by outward radial pressure provided by a balloon or by virtue of self-expanding shape-memory materials such as nickel titanium alloy formulated to transform from martensitic to austenitic phase at body temperature, following delivery by catheter to the desired site. Additionally, the shape-memory materials can be alloyed for later removal by intraluminal catheter flush with cooled saline to induce reversion to a reduced profile at martensitic phase for ease of withdrawal. It should be understood that any know apparatus or method for deploying the stent and balloon pump suitable for the selected body passageway may be used.

In operation an appropriate stent is percutaneously deployed within a desired region of a selected body passageway, the stent having a hollow bore extending longitudinally therethrough. A catheter-based balloon pump is operatively positioned within the hollow bore of the stent. The balloon pump includes a pumping balloon appropriately configured for the desired body passageway. The pumping balloon may also include one or more balloon valves mounted on the catheter as described above. The balloon pump is cyclically inflated and deflated in a known manner to pump fluid in a desired direction through the body passageway.

It should be understood that various changes and modifications of the embodiments shown in the drawings and described in the specification may be made within the spirit and scope of the present invention. For example, because body passageways, including the ascending aorta, vary in size from one person to another, one skilled in the art will recognize that the pumping balloon, balloon valve(s) and stent will necessarily need to be manufactured in a variety of sizes. For instance, while the ascending aorta in most adults is approximately 5.0 centimeters in diameter, other sizes are also common. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A balloon pump system for pumping fluid through a body passageway of a patient, comprising:
   a substantially cylindrical stent, having a hollow bore extending longitudinally therethrough, constructed and arranged to be operatively positioned within a desired portion of the body passageway;
   a catheter configured to be inserted into the body passageway; and
   a balloon pump, mounted on said catheter, constructed and arranged to be operatively positioned within said hollow bore of said stent, said pump being unconnected to and separately positionable with respect to said stent, wherein said stent substantially reduces compliance of the desired portion of the body passageway, thereby improving the efficiency of said fluid pumping therethrough.

2. The system of claim 1, wherein said balloon pump further comprises:
   at least one collapsible and extendable valve operatively coupled to said catheter adjacent to said balloon pump.

3. The system of claim 2, wherein said at least one valve comprises:
   at least one passive valve.

4. The system of claim 2, wherein said at least one valve comprises:
   at least one active valve.

5. The system of claim 4, further comprising a control drive mechanism for collapsing and extending said balloon pump and said at least one valve, wherein said at least one active valve and said pumping balloon are independently controllable.

6. The system of claim 4, wherein said catheter comprises a first lumen fluidically connected to said at least one active valve, and a second lumen fluidically connected to said pumping balloon, wherein said pumping balloon is cyclically inflatable and deflatable, and said at least one active valve is cyclically collapsed and extended, by fluid flow through said first lumen and said second lumen, respectively.

7. The system of claim 4, wherein said at least one active valve is adapted to be electrically controlled.

8. The system of claim 2, wherein said at least one valve is constructed and arranged such that, when fully extended, said at least one valve substantially occludes the desired portion of the body passageway.

9. The system of claim 4, further comprising:
   an extracorporeal controller operatively coupled to said catheter, constructed and arranged to control inflation and deflation of said pumping balloon and to control extension and collapse of said at least one active valve.

10. The system of claim 2, wherein said stent has a length sufficient to enable said pumping balloon and said at least one valve to be operatively positioned within said hollow bore thereof.

11. The system of claim 2, wherein an outer diameter of said balloon pump and an outer diameter of said at least one valve are each approximately equal to an inner diameter of said stent.

12. The system of claim 2, wherein said system is adapted for pumping fluid through a major artery downstream, with respect to normal blood flow, of a natural heart, and wherein said at least one valve comprises:
   a first valve, operatively mounted on said catheter adjacent to said balloon pump so as to be positioned downstream of said balloon pump.

13. The system of claim 12, wherein said at least one valve further comprises:
   a second valve, mounted on said catheter adjacent to said balloon pump so as to be positioned upstream of said balloon pump.

14. An intravascular pumping system for directly pumping blood, comprising:
   a substantially cylindrical intravascular stent adapted to be operatively positioned within a desired portion of a vessel; and
   a balloon pump system comprising:
      a catheter configured to be inserted into the vessel,
      a balloon pump mounted on said catheter and adapted to be operatively positioned within said stent, said pump being unconnected to and separately positionable with respect to said stent; and
      a first collapsible and extendable valve operatively coupled to said catheter adjacent to said balloon pump, said first valve substantially occluding the vessel when substantially extended,
wherein said stent is constructed and arranged to substantially limit compliance of a vessel region in which said balloon pump is located.

15. The intravascular pumping system of claim 14, wherein said catheter comprises:
a first lumen fluidically connected to said first valve; and
a second lumen fluidically connected to said balloon pump,
wherein said first valve and said balloon pump are cyclically inflatable and deflatable by fluid flow through said first and second lumen, respectively.

16. The intravascular pumping system of claim 14, further comprising:
an extracorporeal controller operatively coupled to said catheter, constructed and arranged to control inflation and deflation of said balloon pump and to control expansion and contraction of said first valve.

17. The intravascular pumping system of claim 14, wherein said first valve is operatively positioned within said stent.

18. The intravascular pumping system of claim 15, further comprising:
a second collapsible and extendable valve mounted on said catheter adjacent to said balloon pump, said second valve substantially occluding the vessel when substantially expanded,
wherein said catheter further comprises a third lumen operatively coupled to said second valve.

19. A method for pumping fluid through a vessel, comprising:
a) positioning a substantially cylindrical stent having a hollow bore extending longitudinally therethrough within a desired portion of the vessel, thereby substantially limiting compliance of said desired portion of the vessel;
b) after step a), positioning a balloon pump within said hollow bore of said stent;
c) cyclically inflating and deflating said balloon pump; and
d) preventing said portion of the vessel from significantly expanding and contracting in response to inflation and deflation, respectively, of said balloon pump.

20. A balloon pump system for pumping fluid through a body passageway of a patient, comprising:
a substantially crush-resistant locking stent, having a hollow bore extending longitudinally therethrough, constructed and arranged to be operatively positioned within a desired portion of the body passageway;
a catheter configured to be inserted into the passageway; and
a balloon pump, mounted on said catheter, constructed and arranged to be operatively positioned within said hollow bore of said stent, said pump being unconnected to and separately positionable with respect to said stent, wherein said stent substantially reduces compliance of the desired portion of the body passageway, thereby improving the efficiency of said fluid pumping therethrough.

21. The system of claim 20, wherein said balloon pump further comprises:
at least one collapsible and extendable valve operatively coupled to said catheter adjacent to said balloon pump.

22. The system of claim 21, wherein said at least one valve comprises:
at least one active valve.

23. The system of claim 21, wherein said at least one valve comprises:
at least one passive valve.

24. The system of claim 22, wherein said catheter comprises:
a control drive mechanism for collapsing and extending said balloon pump and said valve, wherein said at least one active valve and said pumping balloon are independently controllable.

25. The system of claim 22, wherein said catheter comprises:
a first lumen fluidically connected to said at least one active valve, and a second lumen fluidically connected to said pumping balloon, and wherein said pumping balloon is cyclically inflatable and deflatable, and said at least one active valve is cyclically collapsed and extended, by fluid flow through said first lumen and said second lumen, respectively.

26. The system of claim 21, wherein said at least one valve is constructed and arranged such that, when extended fully, said at least one valve substantially occludes the desired portion of the body passageway.

27. The system of claim 22, further comprising:
an extracorporeal controller operatively coupled to said catheter, constructed and arranged to control inflation and deflation of said pumping balloon and to control extension and collapse of said at least one active valve.

28. The system of claim 21, wherein said stent has a length sufficient to enable said balloon pump and said at least one valve to be operatively positioned within said hollow bore thereof.

29. The system of claim 21, wherein an outer diameter of said balloon pump and an outer diameter of said at least one valve are each approximately equal to an inner diameter of said stent.

30. The system of claim 21, wherein said system is adapted for pumping fluid through a major artery downstream, with respect to normal blood flow, of a natural heart, and wherein said at least one valve comprises:
a first valve, operatively mounted on said catheter adjacent to said balloon pump so as to be positioned downstream of said balloon pump.

31. The system of claim 30, wherein said at least one valve further comprises:
a second valve, mounted on said catheter adjacent to said balloon pump so as to be positioned upstream of said balloon pump.

* * * * *

UNITED STATES PATENT AND TRADEMARK OFFICE
CERTIFICATE OF CORRECTION

PATENT NO.   : 6,210,318 B1
DATED        : April 3, 2001
INVENTOR(S)  : David M. Lederman It is certified that error appears in the above-identified patent and that said Letters Patent is hereby corrected as shown below:

Column 2,
Line 66, reads "A pumping balloon subsequently" should read -- A pumping balloon is subsequently --

Column 6,
Line 52, reads "balloon pump and stent. In" should read -- balloon pump and stent. In --
Line 56, reads "the stent with" should read -- the stent 350 with --
Line 61, reads "the stent is" should read -- the stent 352 is --

Column 7,
Line 43, reads "balloon 312," should read -- balloon 320, --

Column 9,
Line 62, reads "said pump being" should read -- said pump and catheter being --
Line 65, reads "passage way, thereby improving the efficiency of said fluid pumping there-through." should read -- passageway. --

Column 10,
Line 39, reads "pump and outer diameter of" should read -- pump and said at least one valve are where extended approximately --

Column 11,
Line 33, reads "positioning a substantially" should read -- positioning within a desired portion of the vessel --
Line 34, reads "within a desired portion of the vessel, thereby" should read -- thereby --
Line 38, reads "balloon pump within said" should read -- balloon pump to a desired position within said --
Line 42, reads "and d) preventing said portion" should read -- and wherein said stent prevents said portion --
Line 55, reads "pump being unconnected" should read -- pump and said catheter being --
Line 58, reads "passageway, thereby improving the efficiency of said fluid pumping there-through. should read -- passageway. --

UNITED STATES PATENT AND TRADEMARK OFFICE
CERTIFICATE OF CORRECTION

PATENT NO. : 6,210,318 B1
DATED : April 3, 2001
INVENTOR(S) : David M. Lederman

It is certified that error appears in the above-identified patent and that said Letters Patent is hereby corrected as shown below:

<u>Column 12,</u>
Line 21, reads "a first lumen fluidically connected to said at least" should read -- one or more first lumens each fluidically connected to one of said at least --
Line 26, reads "said first lumen and" should read -- said one or more first lumens and --

Signed and Sealed this

Tenth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,210,318 B1
DATED : April 3, 2001
INVENTOR(S) : David M. Lederman

It is certified that error appears in the above-identified patent and that said Letters Patent is hereby corrected as shown below:

Column 6,
Line 53, reads "the stent has" should read -- the stent 250 has --;
Line 61, reads "the stent 352 is" should read -- the stent 350 is --;
Line 64, reads "the stent is" should read -- the stent 352 is --;

Column 10,
Line 64, reads "pump being" should read -- pump and said catheter being --;

Column 11,
Line 33, reads "positioning within a desired portion of the vessel" should read
-- positioning within a desired portion of the vessel a substantially --;
Line 39, reads "said stent;" should read -- said stent; and --;
Line 42, reads "and wherein said stent prevents said portion" should read -- wherein said stent prevents said portion --;
Line 55, reads "pump and said catheter being" should read -- pump and said catheter being unconnected --

Signed and Sealed this

Seventh Day of October, 2003

JAMES E. ROGAN
*Director of the United States Patent and Trademark Office*